United States Patent [19]

Buschhoff et al.

[11] Patent Number: 4,604,475

[45] Date of Patent: Aug. 5, 1986

[54] METHOD FOR MAKING ORGANOTIN HALIDES

[75] Inventors: Max Buschhoff, Luenen; Wilhelm P. Neumann, Dortmund-Kirchhoerde, both of Fed. Rep. of Germany

[73] Assignee: Schering AG, Berlin and Bergkamen, Fed. Rep. of Germany

[21] Appl. No.: 713,486

[22] Filed: Mar. 19, 1985

[30] Foreign Application Priority Data

Mar. 30, 1984 [DE] Fed. Rep. of Germany ....... 3411834

[51] Int. Cl.$^4$ .............................................. C07F 7/22
[52] U.S. Cl. ...................................................... 556/97
[58] Field of Search .......................................... 556/97

[56] References Cited

U.S. PATENT DOCUMENTS

| | | | |
|---|---|---|---|
| 3,248,411 | 4/1966 | Neumann et al. | 556/97 |
| 3,251,871 | 5/1966 | Dörfelt | 556/97 |
| 3,297,732 | 1/1967 | Banks | 260/429.7 |
| 3,415,857 | 12/1968 | Albert et al. | 556/97 |
| 3,459,779 | 8/1969 | Neumann | 556/97 |
| 4,282,165 | 8/1981 | Liauw et al. | 556/97 |

FOREIGN PATENT DOCUMENTS

| | | |
|---|---|---|
| 1177158 | 9/1964 | Fed. Rep. of Germany . |
| 1962301 | 5/1971 | Fed. Rep. of Germany . |
| 1038838 | 8/1966 | United Kingdom . |

*Primary Examiner*—Helen M. S. Sneed
*Attorney, Agent, or Firm*—Curtis, Morris & Safford

[57] ABSTRACT

A method for making organotin halides of the formula $R_3SnX$, $R_2SnX_2$, or $RSnX_2$ by the redistribution of appropriate mixtures of organotin compounds in the presence of stannous fluoride as a catalyst.

5 Claims, No Drawings

METHOD FOR MAKING ORGANOTIN HALIDES

The present invention relates to a method for making organotin halides of the formula $R_3SnX$, $R_2SnX_2$, or $RSnX_3$ by the redistribution of appropriate mixtures of organotin compounds of the type $R_4Sn$, $R_3SnX$, or $R_2SnX_2$ and tin halide compounds of the type $R_2SnX_2$, $RSnX_3$, or $SnX_4$, where R is alkyl having from 1 to 16 carbon atoms, cycloalkyl, aryl, or aralkyl, and X is one of the halides Cl, Br, and I. Many reactions of this type are known. Some of them in which R is preferably butyl, isobutyl, octyl, or phenyl and X is chlorine are of considerable commercial importance. Frequently these are complex multistep reactions. For example, steps (1) and (2) are part of reaction (3), which is carried out on a large industrial scale:

(1) $R_4Sn + SnCl_4 \rightarrow R_3SnCl + RSnCl_3$
(2) $R_3SnCl + RSnCl_3 \rightarrow 2R_2SnCl_2$
(3) $R_4Sn + SnCl_4 \rightarrow 2R_2SnCl_2$ While reaction (1) proceeds rapidly at room temperature and is exothermal, this is not the case with reaction (2). Rather, the latter proceeds very slowly so that long-time heating at high temperatures is required, for example for seven hours at 220° C. when R is butyl. A reduction of the time and temperature would make the process much more economical through considerable energy savings and thus would represent a highly desirable and substantial technical advance.

This is true also of the following reactions:

(4) $R_4Sn + 2RSnCl_3 \rightarrow 3R_2SnCl_2$
(5) $2R_4Sn + RSnCl_3 \rightarrow 3R_3SnCl$
(6) $R_4Sn + R_2SnCl_2 \rightarrow 2R_3SnCl$
(7) $2R_3SnCl + SnCl_4 \rightarrow 3R_2SnCl_2$ The redistributions (4) and (7) also require going through the slow reaction step (2). All of these reactions are of potential or actual commercial importance, depending on the available starting materials. This holds true also for the other halides mentioned above.

Processes for the preparation of $RSnX_3$ compounds play a special role since, here, individual reaction steps proceed extremely slowly, if at all, with heating alone. The step (8) $R_4Sn + 3SnCl_4 \rightarrow 4RSnCl_3$, for example, can be carried out only with aryl or vinyl compounds, but not with the commercially far more important alkyl or cycloalkyl compounds.

The reason for this is that step (9) $R_2SnCl_2 + SnCl_4 \rightarrow 2RSnCl_3$ will not proceed in these cases.

A departure from the exact stoichiometry in the equations given above can be deliberately made to result in mixtures of organotin halides, for example $R_3SnX$ and $R_2SnX_2$, or $R_2SnX_2$ and $RSnX_3$. Mixtures of the latter type, for example, are commercially important for further processing as stabilizers for plastics.

Because of its foreseeable commercial importance, attempts have been made to carry out reaction (8) by the use of large quantities of phosphorus oxychloride or phosphorus pentachloride, for example. (See German patent 11 77 158.) However, because of the complicated *modus operandi* and the high prices of the auxiliary materials, this process is of no commercial importance.

This most unsatisfactory situation has led to many efforts to make worthwhile those redistribution reactions which proceed slowly or will not occur at all by the use of catalysts. However, all prior proposals have significant basic or technical disadvantages. For example, U.S. Pat. No. 3,297,732 proposes that a group of metal halides be used as catalysts for this purpose, aluminum trichloride being preferred. However, it is known that $AlCl_3$ can be alkylated by organotin compounds, with an attendant loss of alkyl groups. Moreover, the reaction product then is black and difficult to purify. The necessary purifying operations result in losses of material. Furthermore, the described purification by recrystallization from hexane is complicated and largely offsets any advantages, especially since there is no assurance that the product will indeed be free of aluminum compounds that would prove troublesome in later use.

To overcome these drawbacks, published German patent application No. DAS 19 62 301, though using the same or similar catalysts, seeks to eliminate these difficulties by employing an additional and likewise complicated step of hydrolysis with water for separating the reaction products from the catalyst. This process is of dubious value since residual monobutyltin trichloride is completely soluble in water and the tributyltin chloride which is present in small amounts further gives rise to waste water problems. In each case there is a loss of material. Besides, the catalysts named in the prior art are usually suitable only for one-time use and are discarded after working up, which again poses disposal problems and entails additional costs.

It has now been found that stannous fluoride will greatly accelerate, in a particularly advantageous manner, the slow reaction steps mentioned above and that it possesses better activity than prior art catalysts.

The invention, thus, pertains to a method for making organotin halides by the redistribution of appropriate mixtures of organotin compounds of the type $R_4Sn$, $R_3SnX$, or $R_2SnX_2$ and tin halide compounds of the type $R_2SnX_2$, $RSnX_3$, or $SnX_4$ wherein stannous fluoride is used as a catalyst. The reaction is preferably carried out at a temperature above about 210° C. in a homogenous phase, the catalyst being advantageously added in amounts of about 0.01 to 1 mole percent, based on the number of moles of the starting materials.

In a further variant of the process of the invention, the reaction is carried out at temperatures of about 140° to 200° C. in a nonhomogenous phase. The catalyst then is added in amounts of about 5 to 50 mole percent, based on the number of moles of the starting materials.

In still another variant of the process, the reaction mixture is continuously passed over the catalyst.

The method of the invention is suited for the preparation of organotin halides of the general formula $R_3SnX$, $R_2SnX_2$, or $RSnX_3$ by redistribution of appropriate mixtures of organotin compounds of the type $R_4Sn$, $R_3SnX$, or $R_2SnX_2$ and tin halide compounds of the type $R_2SnX_2$, $RSnX_3$, or $SnX_4$. R may be alkyl having from 1 to 16 carbon atoms, methyl, ethyl, n-butyl, n-octyl and n-dodecyl in particular being preferred and of special interest. Examples of branched alkyl groups are isobutyl and 2-ethylhexyl, while cyclohexyl in particular is illustrative of cyclic alkyl groups. R may further stand for aryl, and particularly for phenyl and naphthyl, as well as for aralkyl, for example, tolyl or neophyl (2-methyl-2-phenyl-propyl).

X is one of the halides I, Br, and Cl, Cl being preferred.

Examples of organotin compounds of the types $R_2SnX_2$, $RSnX_3$ and $SnX_4$ are:

n—$C_4H_9SnCl_3$, $SnCl_4$, i—$C_3H_7SnCl_3$, i—$C_4H_9SnCl_3$, n—$C_3H_7SnCl_3$, n—$C_8H_{17}SnCl_3$, (i—$C_4H_9)_2SnCl_2$,
n—$C_5H_{11}SnCl_3$, (n—$C_8H_{12})_2SnCl_2$,
(n—$C_3H_7)_2SnCl_2$,
(n—$C_4H_9)_2SnCL_2$, $SnBr_4$, $(C_{12}H_{25})_2SnCl_2$,
chx$SnCl_3$,
(cHx=cyclohexyl), (n—$C_4H_9)_2SnBr_2$, $C_6H_5SnCl_3$, $C_6H_5CH_2SnCl_3$, neophyl $SnI_3$, chx$SnBr_3$, cHx$SnI_3$.

Examples of tin compounds of the types $R_4Sn$, $R_3SnX$ and $R_2SnX_2$ are:

(n—$C_3H_7)_2SnCl_2$, (cHx$)_2SnCl_2$, (n—$C_{12}H_{25})_3SnCl$, (i—$C_4H_9)_2SnCl$, $(C_6H_5CH_2)_2SnCl_2$, (n—$C_{12}H_{25})_4Sn$, $(C_6H_5)_2SnCl_2$, (i—$C_3H_7)_2SnCl_2$, (n—$C_8H_{17})_3SnCl$, (n—$C_8H_{17})_4Sn$, (n—$C_4H_9)_3SnCl$, (n—$C_4H_9)_2SnBr_2$, $(C_6H_5)_3SnCl$, (i—$C_4H_9)_3SnCl$, (cHx$)_3SnCl$, (n—$C_4H_9)_3SnBr$, $(C_6H_5)_4Sn$, (n—$C_4H_9)_4Sn$, $(C_6H_5CH_2)_3SnCl$.

The advantageous action of the catalysts used in accordance with the invention will now be illustrated with data using as an example reaction (2) in a non-homogenous phase, which proceeds slowly. However, with the catalysts indicated (20 mole percent), and without a solvent, the reaction is accelerated as follows:
Without catalyst: 140° C., 50 hours, 75% conversion
With $SnF_2$: 140° C., 4 hours, 97% conversion The $SnF_2$ used in accordance with the invention results in a significantly accelerated reaction rate also in comparison with the metal chlorides named in the prior art, as indicated by the following values:
Reaction (2), R=n-butyl, 20 mole percent catalyst
$SnCl_2$: 140° C., 24 hours, 81% conversion
$HgCl_2$: 140° C., 6 hours, 75% conversion
$PbCl_2$: 140° C., 24 hours, 80% conversion
$PbF_2$: 140° C., 4 hours, 74% conversion As can be seen from the values for $PbF_2$, given for comparison, this compound results in a faster reaction than the metal chlorides but falls short of yielding the outstanding values of $SnF_2$, whose advantageous properties are further demonstrated by the following data:
Reaction (4), R=n-butyl, 15 percent catalyst
Without catalyst: 140° C., 24 hours, 74% conversion
$SnCl_2$: 140° C., 24 hours, 97% conversion
$SnF_2$: 140° C., 4 hours, 97% conversion The same can be shown for reaction (5), with R being n-butyl, for example:
Without catalyst: 140° C., 7 hours, 40% conversion
$SnCl_2$: 140° C., 7 hours, 90% conversion
$SnF_2$: 140° C., 2 hours, 97% conversion The reaction step according to equation (6) is also very considerably accelerated (with R being n-butyl):
Without catalyst: 150° C., 50 hours, 35% conversion
$SnCl_2$: 150° C., 9 hours, 90% conversion
$SnF_2$: 140° C., 3 hours, 96% conversion Similar results are obtained with other radicals, for example, when R is n-octyl.

A special advantage of this novel catalysis is that the reaction step according to equation (9), which without a catalyst will not occur at all with the commercially particularly important aliphatic groups present on tin, now is made possible and will proceed in a very useful manner (R=n-butyl):
Without catalyst: 180° C., 5 hours, 0% conversion
$SnF_2$: 180° C., 5 hours, 70% conversion As a result, reaction (8), which up to now was not feasible but is highly desirable from a practical point of view, now can be readily performed (R=n-butyl). The 25 percent conversion obtained without a catalyst corresponds to reaction step (1), after which, however, no further conversion occurred in the past and the usability of the reaction thus ceased.
Without catalyst: 150° C., 20 hours, 25% conversion
$SnCl_2$: 150° C., 21 hours, 97% conversion
$SnF_2$: 140° C., 2 hours, 70% conversion In each of the cases given by way of example, complete conversion can, of course, be obtained in accordance with the invention until thermodynamic equilibrium is established.

When the process of the invention is carried out at a temperature below 210° C., the melting point of $SnF_2$, the reaction obviously is heterogeneous, with the reaction rate then depending on the surface area of the solid catalyst and, in the case of constant surface area per unit weight, also on the quantity of the catalyst. For example, the reaction according to equation (2), with R=n-butyl, at 160° C. and in four hours is carried out with 5 mole percent $SnF_2$ to a net yield of 70 percent, and with 20 mole percent to a net yield of 96 percent. Depending on the degree of distribution, that is, the ratio of surface area to unit weight, the same effect can be obtained with both larger and smaller quantities of catalyst. This is true also of a catalyst which is deposited in finely divided form on a carrier material. Depending on the working-up method, described further on, it may be advantageous to use a larger quantity of a coarse grained catalyst or a smaller quantity of a very finely divided catalyst.

Technical $SnF_2$ has the same activity as reagent grade $SnF_2$. Special drying prior to use to prevent hydrolysis of the organotin halide is recommended but is not essential.

The organotin product is readily separated from the solid catalyst. The $SnF_2$ can be simply filtered or centrifuged off, or the product can be siphoned off from the settled catalyst. Solvents are not required for the process or for the separation but will do no harm. For separation of the catalyst, the temperature of the mixture is advantageously maintained above the melting point of the product, for example, at 50° C. in the case of the commercially important di-n-butyltin dichloride. The product may also be distilled off the catalyst, optionally under vacuum.

A special advantage of carrying out the process in a nonhomogeneous phase is that the catalyst can be reused without further processing. It may be particularly advantageous to retain the catalyst in the reaction vessel, for example, after siphoning or reverse filtering off the liquid product. In principle, the catalyst can be reused any number of times.

The process may also be carried out continuously, with the reaction mixture being conducted at appropriate temperatures over a fixed bed of catalyst or through a column packed with $SnF_2$.

Carrying out the process in a homogeneous phase offers the advantage that considerably smaller quantities of catalyst will be required.

As with operation in a nonhomogeneous phase, the catalyst can be readily separated after cooling to a temperature below 210° C. However, since smaller quantities of the catalyst are added in homogeneous operation, separation of the catalyst can usually be dispensed with.

Catalysis in a homogenous phase is feasible when the reaction temperature is held above the melting point of $SnF_2$, at about 210° C., and increased thermal stresses on the reaction mixture can be tolerated. Of course, such stresses will be of relatively short duration since at that temperature reaction equilibrium will be established after about one hour.

The nature of the invention will now be further elucidated in terms of the preparatory reactions described in the Examples which follow, wherein Bu=n-butyl, Me=methyl, Ph=phenyl, Oc=octyl, and cHx=cyclohexyl.

EXAMPLES 1 (a), (b) AND (c)

14.0 g of $Bu_4Sn$ first mixed with 2.5 g of finely powdered, dry $SnF_2$ and then with 10.5 g of $SnCl_4$ (exothermal reaction). The mixture is heated with stirring to 160° C., held at that level for 6 hours, and then worked up by distilling it off the catalyst (boiling point, 91° to 93° C.; 0.1 mm Hg). Yield: 22.1 g n-$Bu_2SnCl_2$=90%. Further amounts of product are allowed to remain on the catalyst to prevent its overheating.

The catalyst is retained in the vessel and the amounts of $Bu_4Sn$ and $SnCl_4$ indicated are added once more and the above procedure is followed. Yield: 23.6 g=96%. This is repeated twice with the same yields (up to 98%) without loss of catalyst activity.

The product may also be filtered off the catalyst above the melting point of the product, for example, at from 50° to 60° C.

The above procedure is followed but with 7.2 g of $Me_4Sn$ in place of the $Bu_4Sn$. The product is filtered off the catalyst at 120° C. and $Me_2SnCl_2$, which solidifies immediately (melting point, 107° C.), is obtained.

The same procedure is employed to prepare $Ph_2SnCl_2$ by introducing 50.0 g of $Ph_4Sn$ gradually, with stirring, into 30.6 g of $SnCl_4$ and bringing the mixture to readily stirrable consistency by further heating, if necessary. 6.0 g of $SnF_2$ are then added and the mixture is heated for 5 hours to 140° C. and filtered off the catalyst as above. This yields 75 g $Ph_2SnCl_2$=93%, Melting point, 41° C.

EXAMPLE 2

Similarly, 3.48 g of $Bu_4Sn$, 5.66 g of $BuSnCl_3$, and 1.25 g of $SnF_2$ after 3 hours at 150° C. yield 8.8 g (=97%) of $Bu_2SnCl_2$. The same result is obtained with 2.5 g of $SnF_2$ after 1.5 hours and with 0.70 g after 5 hours.

EXAMPLES 3 (a), (b) AND (c)

In the same way, 6.96 g of $Bu_4Sn$, 2.48 g of $BuSnCl_3$, and 1.25 g of $SnF_2$ after 2 hours at 140° C. yield 9.15 g (=97%) of $Bu_3SnCl$.

A comparable result is obtained after 2.8 hours when the same amount of iso$Bu_4Sn$ is used in place of $Bu_4Sn$, and of iso$BuSnCl_3$ in place of $BuSnCl_3$.

Similarly, 10.5 of iso$Oc_4Sn$ (isoOc=2 ethylhexyl) and 3.4 g of iso$OcSnCl_3$ after 3 hours yield 14.2 g (=96%) of iso$Oc_3SnCl$.

In place of the $BuSnCl_3$ mentioned initially an equimolar amount of $BuSnBr_3$ may be used to give $Bu_3SnBr$ in the same manner, but after 2.5 hours.

EXAMPLE 4 (a), (b) AND (c)

15.8 g (=70%) of $BuSnCl_3$ are obtained from 6.94 g of $Bu_4Sn$, 15.66 g of $SnCl_4$, and 2.51 g of $SnF_2$ after 2 hours at 140° C., followed by fractionation.

1.25 g of $SnF_2$, 8.32 g of n—$Oc_2SnCl_2$, and 5.24 g of $SnCl_4$ yield 49.5% of n—$OcSnCl_3$ in addition to 50% of n—$Oc_2SnCl_2$ after 1 hour at 100° C.

EXAMPLE 5

15.2 g of $Bu_2SnCl_2$ and 3.14 g of $SnF_2$ are stirred into 17.35 g of $Bu_4Sn$, the mixture is heated for 3 hours at 140° C., and 31.25 g (=96%) $Bu_3SnCl$ are obtained.

With 3.80 g of $SnCl_2$ as the catalyst, a yield of 90% is obtained only after 9 hours, even at 150° C.

EXAMPLES 6 (a) AND (b)

11.4 g of $BuSnCl_3$ and 3.9 g of finely powdered $SnF_2$ are heated to 160° C. with stirring. 13.1 g of $Bu_3SnCl$ are then added and the mixture is stirred for 6 hours at that temperature. After the usual working up, 23.3 g (=95%) of pure $Bu_2SnCl_2$ is isolated.

The same result is obtained when the same procedure is followed but equimolar amounts of $Bu_4Sn$ and $SnCl_4$ are used with the addition of $SnF_2$.

EXAMPLES 7 (a) AND (b)

13.1 g of $Bu_3SnCl$, 2.5 g of $SnF_2$, and 11.4 g of $BuSnCl_3$ are heated for 4 hours at 160° C. After washing of the catalyst with n-hexane and evaporation of the solvent, 23.8 g (=97%) of $Bu_2SnCl_2$ are isolated. The catalyst is used three more times and even then exhibits no loss of activity.

When the amounts, temperatures, and time are as above, but 5.7 g of finely powdered $NaSn_2F_5$ is used in place of $SnF_2$, the first reaction yields merely 61% of $Bu_2SnCl_2$, but also 12% of $Bu_3SnCl$, 9% of $BuSnCl_3$ and 18% of lower- and higher-boiling unidentified by-products. Further reactions produce no improvement.

EXAMPLES 8 (a) AND (b)

16.93 g of n-$OcSnCl_3$ are mixed with 3.14 g of dry, finely ground $SnF_2$ and heated with stirring to 80° C. Then 24.67 g of n-$Oc_3SnCl$ are added and the mixture is heated gradually, over 1 hour, to a higher level so that in the end 205° C. is reached for a short time. After filtering off the catalyst, washing thereof with n-hexane, and working up all solvent fractions, 41.5 g of n—$Oc_2SnCl_2$ are obtained, which represent a yield of 99.8%.

By the same procedure, but using 3.8 g of $SnCl_2$ as the catalyst, comparable yields are obtained only after 3 hours, along with 1% each of the two starting materials.

EXAMPLES 9 (a), (b) AND (c)

Similarly, 6.52 g of $Bu_3SnCl$ with 1.57 g of $SnF_2$ and 2.62 g of $SnCl_4$ yield 8.7 g (95%) of $Bu_2SnCl_2$ after 6 hours at 160° C.

When 9.87 g of n-$Oc_3SnCl$ are similarly mixed with 2.62 g of $SnCl_4$ and 2.5 g of $SnF_2$ and the mixture is heated to a higher level so that after 1 hour 205° C. is reached, and that temperature is maintained for 0.5 hour with stirring, then n-$Oc_2SnCl_2$ is obtained in a quantitative yield. (Demonstrated: 12.45 g=99.8%).

For the analogous preparation of dineophyltin dibromide, 43.9 g of $SnBr_4$ are melted, 119.6 g of neophyl$_3SnBr$ and 9.0 g of $SnF_2$ are introduced, and the mixture is stirred for 4 hours at 140° C.

EXAMPLE 10

135.3 g of $cHx_4Sn$ are gradually introduced into a mixture of 26.1 $SnCl_4$ and 31.4 g $SnF_2$ and the mixture is heated further with vigorous stirring until it is readily stirrable. If is then maintained at 140° C. to 145° C. for 1.5 hours and the product is filted off the catalyst at that temperature. 139 g=(86%) of $cHx_3SnCl$, melting point 129° C., and another 17 g are obtained after washing the catalyst with cyclohexane, making a total of 156 g=96.6%. Such washing can be dispensed with when starting material is again passed over the catalyst.

EXAMPLE 11

104.1 g of $Bu_4Sn$ are mixed with 26.1 g of $SnCl_4$ (exothermal reaction) and the hot mixture is conducted through a heated quartz column with an inside diameter of 20 mm which is filled to a height of 10 cm with $SnF_2$ of medium particle size. The filling is maintained at 200° C. by external heating and the discharge rate is regulated by means of a subjacent frit so that $Bu_3SnCl$ leaves the column in the desired purity. If small amounts of $Bu_4Sn$ and $Bu_2Sn$ and $Bu_2SnCl_2$ can be tolerated, the throughput may be accelerated. The process can be made continuous by having the feed enter through metering means and a mixing chamber at the top of the column.

EXAMPLES FOR REACTIONS IN A HOMOGENOUS PHASE

EXAMPLES 12 (a) AND (b)

A mixture of 80 g of $Bu_3SnCl$, 66.6 g of $BuSnCl_3$, and 0.075 g of $SnF_2$ (0.1 mole percent) is heated to 215° C. with stirring.

The composition of the reaction mixture is reported below as a function of time:

|          | $BuSnCl_3$ | $Bu_2SnCl_2$ | $Bu_3SnCl$ |
|----------|------------|--------------|------------|
| 0.5 hour | 2.6 mole % | 93.4 mole %  | 4.0 mole % |
| 1 hour   | 1.6 mole % | 96.7 mole %  | 2.3 mole % |
| 2 hours  | 0.7 mole % | 97.1 mole %  | 2.2 mole % |

A test run in the same manner but with 0.01 mole percent $SnF_2$ produces a similar result.

EXAMPLES 13 (a) AND (b)

106.3 g of $Bu_4Sn$ (technical grade containing 1.9% Cl) and 70 g of $SnCl_4$ are mixed with 0.09 g of $SnF_2$ and heated to 215° C. with stirring. After 2 hours, the reaction mixture comprises 2.5 mole percent of $BuSnCl_3$, 97 mole percent of $Bu_2SnCl_2$, and 0.5 mole percent of $Bu_3SnCl$.

104.6 g of $Oc_4Sn$ (technical grade containing 2.3% Cl) and 44 g of SnCl are similarly reacted with 0.06 g $SnF_2$. After 2 hours, the reaction product comprises 7.4 mole percent of $OcSnCl_4$, 92.1 mole percent of $Oc_2SnCl_2$, and 0.5 mole percent of $Oc_3SnCl$.

We claim:

1. A method for making an organotin halide of the formula $R_3SnX$, $R_2SnX_2$, or $RSnX_3$, or a mixture of two or more of such halides, wherein R is saturated hydrocarbon and X is halide, which comprises redistributing an appropriate mixture of an organotin compound of the type $R_4Sn$, $R_3SnX$, or $R_2SnX_2$ with a tin halide of the type $R_2SnX_2$, $RSnX_3$, or $SnX_4$ in a homogeneous phase at a temperature above about 210° C. in the presence of stannous fluoride as a catalyst.

2. A method for making an organotin halide of the formula $R_3SnX$, $R_2SnX_2$, or $RSnX_3$, or a mixture of two or more of such halides, wherein R is saturated hydrocarbon and X is halide, which comprises redistributing an appropriate mixture of an organotin compound of the type $R_4Sn$, $R_3SnX$, or $R_2SnX_2$ with a tin halide of the type $R_2SnX_2$, $RSnX_3$, or $SnX_4$ in a nonhomogeneous phase at a temperature of about 140° C. to 200° C. in the presence of stannous fluoride as a catalyst.

3. A method as in claim 1, wherein the catalyst is present in an amount of about 0.01 to 0 mole percent, based on the number of moles of the starting materials.

4. A method as in claim 2, wherein the catalyst is present in an amount of about 5 to 50 mole percent, based on the number of moles of the starting materials.

5. A method as in claim 2, wherein the reaction mixture is continuously conducted over the catalyst.

* * * * *